United States Patent [19]

Nielsen

[11] 4,416,854

[45] Nov. 22, 1983

[54] METHOD FOR KILLING WATER BORNE MICROORGANISMS

[75] Inventor: James W. Nielsen, Newport, Oreg.

[73] Assignee: Sharon G. Nielsen, Newport, Oreg.; a part interest

[21] Appl. No.: 479,192

[22] Filed: Mar. 29, 1983

Related U.S. Application Data

[63] Continuation of Ser. No. 346,735, Feb. 8, 1982, abandoned, which is a continuation of Ser. No. 164,238, Jun. 30, 1980, abandoned, which is a continuation-in-part of Ser. No. 69,291, Aug. 24, 1979, Pat. No. 4,276,732.

[51] Int. Cl.$^3$ ............... A61L 2/16; A61L 2/18; E03D 9/03; C02F 1/50
[52] U.S. Cl. .................................. 422/29; 4/228; 204/148; 210/764; 422/266; 424/131; 424/140; 424/145
[58] Field of Search ............... 422/28, 29, 266, 267, 422/265; 4/226, 228, 231; 424/131, 140, 145; 204/147, 148; 210/764

[56] References Cited

U.S. PATENT DOCUMENTS

| | | | |
|---|---|---|---|
| 2,329,429 | 9/1943 | Weaver | 422/277 X |
| 3,479,130 | 11/1969 | Rapaport | 422/29 X |
| 3,494,727 | 2/1970 | Rapaport | 422/29 X |
| 3,513,586 | 5/1970 | Meyer et al. | 43/124 |
| 3,604,020 | 9/1971 | Moisa | 4/228 |
| 3,677,408 | 7/1972 | Dinizo | 422/266 X |
| 3,869,069 | 3/1975 | Levey et al. | 4/228 X |
| 4,202,858 | 5/1980 | Bruce et al. | 422/29 X |
| 4,217,331 | 8/1980 | Schaub | 422/277 X |

Primary Examiner—Barry S. Richman
Attorney, Agent, or Firm—Klarquist, Sparkman, Campbell, Leigh & Whinston

[57] ABSTRACT

A method for killing water borne microorganisms comprises reacting two electrolytically-reactive elemental metals in water to dissolve sufficient metal ions to kill algae and coliform bacteria, without making the water unsafe for human use. Lead, copper and zinc are examples of such metals. Apparatus for performing the method comprises a perforated container of chips of such metals. A small version of the device can be used in toilet reservoirs to prevent the growth of microorganisms within the toilet bowl. A larger version of the device, submerged in a swimming pool, effectively prevents the growth of algae or coliform bacteria, substantially reducing or eliminating the need for chlorine. One embodiment of the device has an elongated cylindrical container with perforated side and bottom walls and a hook at its upper end for suspending the device in a swimming pool or toilet reservoir. A second embodiment of the device has a vertically elongated, broad-based container with only a lower portion of its side walls perforated. An air bubble retained inside the container when immersed in water helps keep the container upright.

4 Claims, 5 Drawing Figures

U.S. Patent     Nov. 22, 1983     4,416,854
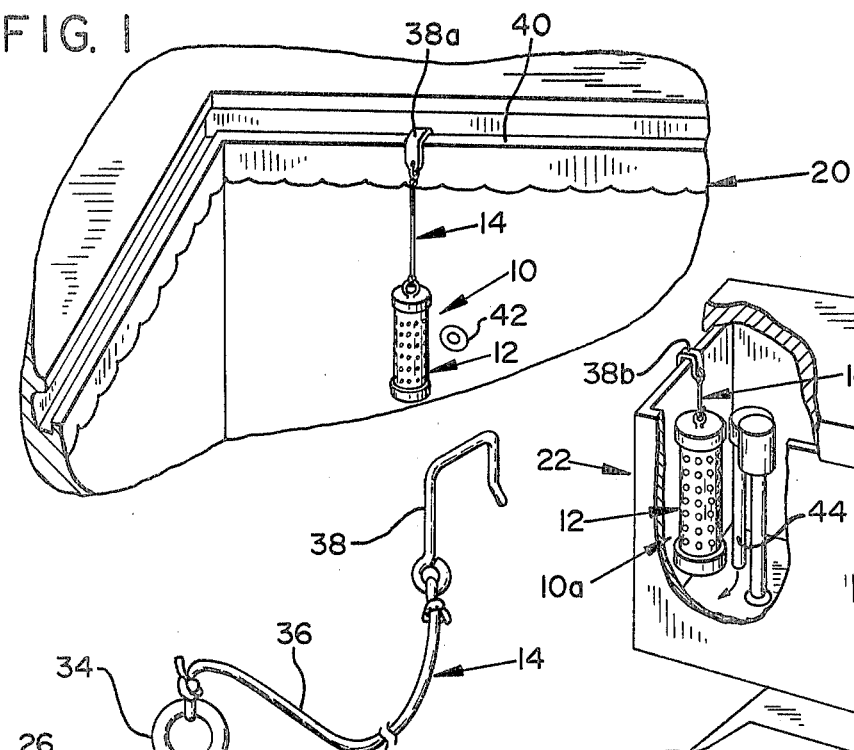
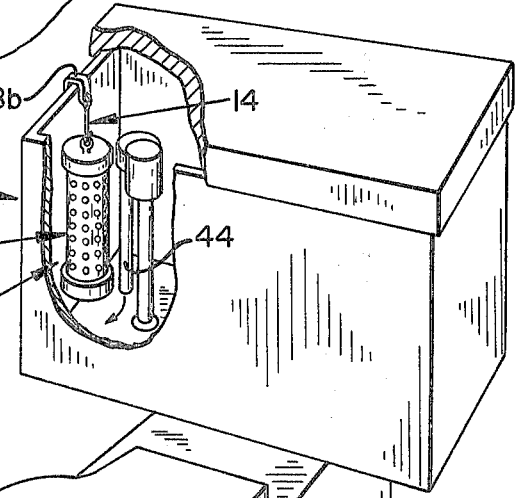
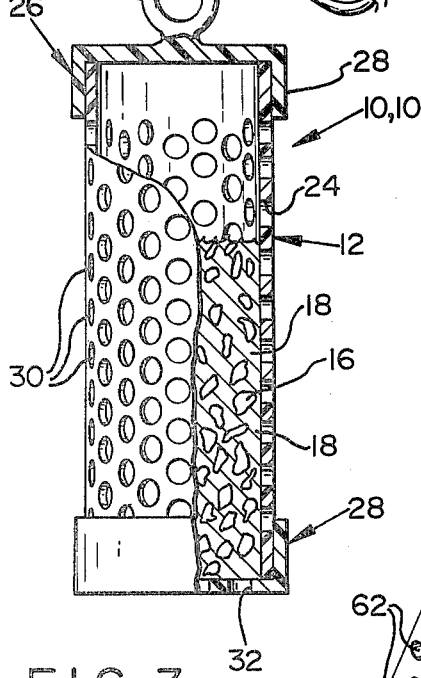
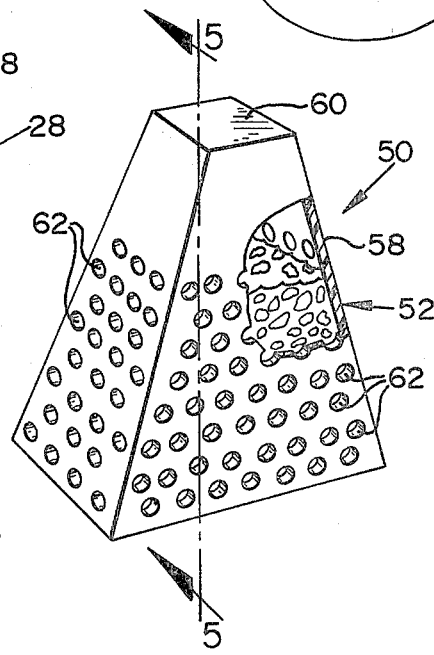
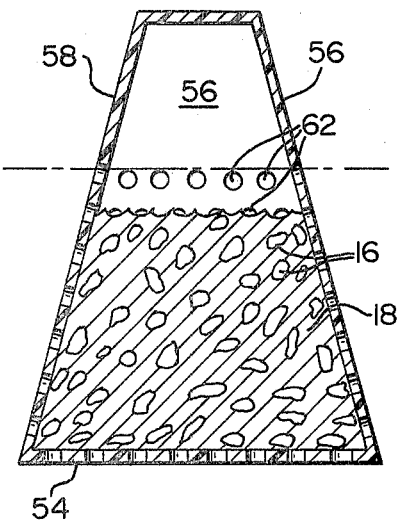

METHOD FOR KILLING WATER BORNE MICROORGANISMS

This application is a continuation of application Ser. No. 346,735 filed Feb. 8, 1982, and now abandoned, which is a continuation of application Ser. No. 164,238 filed June 30, 1980, and now abandoned, which is in turn a continuation-in-part of application Ser. No. 069,291, filed Aug. 24, 1979, entitled "Device For Killing Moss," now U.S. Pat. No. 4,276,732 issued July 7, 1981.

BACKGROUND OF THE INVENTION

The invention relates generally to apparatus for cleaning swimming pools, toilets and the like, and more particularly to methods and apparatus for producing biocidal solutions for killing microorganisms in bodies of water.

Control of algae and bacteria growths in swimming pools is a serious problem. Most modern swimming pools are heated, exposed to sunlight and are substantially closed recirculating systems, making them an ideal place for algae to grow. Users of such pools introduce coliform (*E. coli*) and other bacteria into the pool water. They also shed skin and hair in the pool water, and occasionally urinate in the pool, providing a fertile environment for bacteria to multiply rapidly. Thus, it is necessary to control the growth of both algae and bacteria in swimming pools. Conventionally, this requires the addition of large amounts of chlorine to the pool. However, the chlorine tends to burn the swimmers' eyes, particularly if used in quantities sufficient to suppress the growth of algae. The chlorine vaporizes quickly, producing an unpleasant odor. To maintain proper chlorine levels, daily replenishment is required. This can be very expensive and troublesome. Consequently, many pool owners often fail to maintain sufficient chlorine levels to suppress algae and bacteria growth, necessitating frequent cleaning of the pool and creating a health hazard to pool users.

Maintaining the cleanliness of toilet bowls is another difficult problem. Fecal matter and urine contaminate the bowl and provide a fertile feed stock for bacteria therein. If a toilet bowl is not cleaned frequently, a scum develops within the bowl below the water line. This scum includes coliform and other bacteria and varieties of algae that require little or no light in which to grow. Conventionally, toilet bowls are frequently scrubbed and disinfected to eliminate the scum build up and to kill the bacteria and other microorganisms that grow in the bowl. Another approach has been to try to prevent the build up of scum or the growth of bacteria by adding chlorine to the toilet bowl water. One such device, containing stabilized, solidified chlorine, is immersed in the toilet reservoir to dissolve chlorine into the toilet water. However, such devices are relatively short lived, six months at most. Thus, their continued use over an extended period of time can become rather expensive.

Certain metal compounds, such as copper sulfate, are known to have biocidal characteristics. Copper sulfate powders have been used on roof tops to kill moss. Copper sulfate crystals have also been dissolved in bodies of water such as ponds or lakes to curtail the growth of algae. However, the copper sulfate quickly dissolves into the water and then dissipates as the water in the pond is replaced by additional water. It also does not appear that copper sulfate or similar compounds can be used safely in swimming pools or other bodies of water in quantities sufficient to kill algae and coliform bacteria and yet safe for human use. It is unknown whether copper sulfate has ever been tried in toilets. However, it is apparent that the copper sulfate, if so used, would have to be replenished each time the toilet is flushed. It would be preferable to have a device that would continually act to kill algae and bacteria over a long period of time without having to be replenished and without endangering users of the water.

S. L. Rapaport has previously proposed, in U.S. Pat. Nos. 3,479,130 and 3,494,727, the use of two metals, such as copper and lead, on roof tops to inhibit microbial or fungal growths which darken roof tops in semi-tropical and tropical climates. An electrolytic action results when rainwater contacts the metals to dissolve metal ions and thereby create a solution which kills the microbes and fungus. However, Rapaport does not disclose the use of elemental metals in swimming pools, toilet bowls or other bodies of water. Nor does Rapaport disclose use of such metals to kill algae or coliform bacteria in toilets or swimming pools. Therefore, there remains a need for a means for killing microorganisms in bodies of water without rendering the water unsafe for human use.

SUMMARY OF THE INVENTION

One object of the invention is to provide a device which will effectively kill algae and bacteria in bodies of water.

Another object of the invention is to provide means for killing bacteria and algae without rendering the water unusable by humans.

A further object of the invention as aforesaid is to substantially reduce or eliminate the need for chlorinating bodies of water, such as swimming pools and toilet bowls, while effectively preventing the growth of algae and coliform bacteria.

An additional object is to provide a method for suppressing the growth of microorganisms in swimming pools and toilet bowls which does not require the use of chlorine.

A further object is to provide a method as aforementioned which is compatible with conventional plumbing systems.

Yet another object is to provide a method as aforementioned which is simple, inexpensive and long-lasting in effect.

A specific object of the invention is to provide a device which can be inconspicuously submerged in a swimming pool to produce a biocidal solution which will effectively prevent the growth of algae and coliform bacteria therein without rendering the water unsafe for humans.

Another specific object of the invention is to provide a device which can be placed in a toilet reservoir to produce a biocidal solution which will effectively prevent the buildup of scum and growth of bacteria in toilet bowls.

Yet another object is to provide a device as aforementioned which will continue to remain effective for a number of years without replenishment.

According to the invention, a method for killing microorganisms in a body of water comprises electrolytically reacting two elemental metals in the presence of water to produce metal ions which are effective for killing microorganisms. Only one of such metals is required to produce biocidal ions. However, it is preferable to produce biocidal ions of at least two metals, such as copper and lead, which cooperate to effectively kill algae and bacteria even at very low, safe concentrations of each kind of metal ion. Suitable apparatus for performing the method comprises means for containing the two elemental metals in proximity to one another and means for admitting water into contact with such metals. The metals can be provided in the form of chips mixed together in a perforated container which can be suspended within the body of water to be cleansed. The size of the container and the quantities of metals are adapted to the particular application, whether it be a swimming pool or a toilet bowl reservoir. Preferably, the container is relatively narrow in at least one dimension so that water can flow easily through the container.

The foregoing and other objects, features and advantages of the invention will become more apparent from the following detailed description of several preferred embodiments which proceeds with reference to the drawing.

BRIEF DESCRIPTION OF THE DRAWING

FIG. 1 is a perspective view of a portion of a swimming pool with one embodiment of a device according to the invention suspended in the water from the pool wall.

FIG. 2 is a perspective view of a toilet, with a device of the FIG. 1 embodiment suspended in the toilet reservoir, a portion of which is cut away to show interior detail.

FIG. 3 is an enlarged side elevational view of the device of FIGS. 1 and 2, a portion being cut away.

FIG. 4 is a perspective view of a second embodiment of a device according to the invention, a portion being cut away to show interior detail.

FIG. 5 is a cross-sectional view taken along line 5—5 of FIG. 4.

DETAILED DESCRIPTION

In general, a device for killing water borne microorganisms comprises a perforated container at least partially filled with chips or pieces of at least two elemental metals. The metals are selected to react electrolytically in the presence of water to dissolve ions of such metals into the water. The ions of at least one of the two metals must be biocidal to the specific forms of microorganisms to be controlled. Better yet, the ions of both such metals are biocidal. The preferred embodiment of the invention calls for the use of chips or pieces of copper and lead. It has been found that lead and copper ions effectively kill algae and coliform bacteria both in swimming pools and in toilets. Moreover, the lead and copper ions cooperate to obtain the desired biocidal effect at extremely low concentrations of such ions; concentrations far below those considered safe for human use of the water. Zinc is another elemental metal which can be used in combination with lead to kill water borne algae and bacteria. Many other elemental metals which will react electrolytically in the presence of water are known. Some of these metals, although unnamed herein, are also likely to have biocidal characteristics, and thus come within the teachings of the present invention.

The form of container used in practicing the present invention can be varied with specific applications. FIGS. 1-3 disclose a presently preferred embodiment for use in swimming pools and toilet tanks. FIGS. 4 and 5 show an alternative embodiment of a device according to the invention.

FIG. 1 EMBODIMENT

Referring to FIGS. 1-3, a device 10, 10a for killing microorganisms comprises a perforated container 12, means 14 for suspending the container in a body of water and chips or pieces of copper 16 and lead 18 inside the container. Device 10 is sized for use in a swimming pool 20, as shown in FIG. 1. For a pool containing between 15,000 and 20,000 gallons of water, device 10 contains approximately three pounds of lead and copper chips mixed in approximately equal proportions. Similarly, device 10a is sized for use in a toilet tank 22 as shown in FIG. 2. For a standard-sized tank containing about five gallons of water, device 10a contains approximately three ounces of lead and copper chips, also mixed in approximately equal proportions.

Referring to FIG. 3, a preferred form of container 12 comprises an elongated tube 24 defining a cylindrical side wall, and upper and lower end caps 26, 28 enclosing the ends of tube 24. Container 12 is preferably formed of plastic, but other materials can be used as well. Tube 24 is perforated all around by side wall openings 30 sized for admitting water into the container while retaining the metal chips therein.

The upper and lower end caps are sized to snugly receive the ends of tube 20 and are secured in place by a suitable adhesive. The lower end cap can be provided with openings 32 similar to openings 30. Suspending means 14 is connected to upper cap 26 and includes a connector ring 34, a cord 36 and a hook 38. Referring to FIG. 1, hook 38a is sized to engage the wall 40 of the gutter of swimming pool 20. Referring to FIG. 2, hook 38b is sized to engage the wall of toilet tank 22.

In operation, swimming pool device 10 (FIG. 1) is suspended from the gutter of the swimming pool, preferably in the vicinity of a water outlet 42, and is immersed in the pool water. Contact with the water causes an electrolytic reaction between the different metal chips in the container. Ions of the metals are thereby dissolved into the water and disperse in the pool. The flow of water from outlet 42 provides a continuous circulation of fresh water through openings 30 and into contact with the metallic chips, thereby enhancing the rate the dissolution of metallic ions into the water in the pool. Perspiration of pool users, or urination in the pool water, salinizes the water, increasing the electrolytic action to further enhance the dissolution of metal ions into the water.

EXAMPLE 1

It has been found that a device 10, containing approximately three pounds of lead and copper chips, effectively kills algae and coliform bacteria in swimming pools without endangering swimmers. Populations of such microorganisms remain substantially nil in swimming pools provided with device 10 for many months, even though the pools are used frequently by swimmers, the water temperatures are maintained as high as 90° F. and no chlorine is added.

In several tests, water sample analyses were performed periodically over a three month period commencing approximately one week after immersing device 10 in the pools. The analyses indicated chlorine levels of less than 0.1 milligrams per liter, too low to prevent the growth of algae or bacteria. The analyses also indicated metal ion levels in the range of 0.04 to 0.14 milligrams per liter for copper and detectable amounts of lead, in quantities less than 0.01 to 0.02 milligrams per liter. The lead and copper levels rose into the above-described range within approximately the first week of use. Thereafter, such levels ceased to increase despite the substantially closed nature of the recirculating system. These quantities proved to be sufficient to kill algae and coliform bacteria. Yet they were far less than the maximum amounts of lead and copper that are permissible in water for human consumption. For lead, that maximum amount is 0.50 milligrams per liter and for copper it is 0.75 milligrams per liter.

As a control, similar swimming pools were operated in the same locality, during the same time period and under similar conditions as the foregoing tests, but without device 10. Substantial quantities of algae and bacteria grew in the water of these pools.

One example demonstrates the efficacy of the device 10 in swimming pools. On day 1 device 10 was placed in a pool which had not been chlorinated for several weeks. On that date the chlorine levels in the water were essentially zero. The pool had heavy growths of green and black algae (stonewarts) growing on its walls. A layer of scum floated on the surface of the pool. After seven days, the surface scum was drying up and sedimenting to the bottom of the pool. The green and black algae was peeling from the sides of the pool and also sedimenting to the bottom. On day 14 it was necessary to clean the pool filter to eliminate the dying algae. A bacteriologic water analysis indicated that coliform bacteria were still present. The copper and lead concentrations were 0.14 and less than 0.02 milligrams per liter, respectively. On day 21, following vacuuming of the pool, the pool water was nearly free of algae. After one month, following a second vacuuming, the pool was entirely free of algae. Another month later, the pool was still free of algae and coliform bacteria counts were zero. Copper and lead levels were 0.12 and less than 0.02, respectively.

In view of the test results, it is expected that swimming pool owners could substantially reduce their use of chlorine in swimming pools while still obtaining effective bacteria and algae control. Adequate safety standards can be maintained in a pool in which device 10 is immersed by chlorinating monthly rather than daily as is now required. Substantial savings will thus accrue to pool owners while maintaining pool sanitation standards. At the same time, irritation to swimmer's eyes resulting from contact with chlorinated water will be virtually eliminated.

EXAMPLE 2

Device 10a is suspended from the side wall of toilet tank 22, preferably near water inlet 44, the bottom wall of container spaced above the bottom of the tank. Each time the toilet is flushed, water containing dissolved metal ions empties from tank 22 into the toilet bowl to kill any algae and bacteria therein. The water in container 12 drains out of the container through openings 32. Fresh water flowing from inlet 44 then refills the tank and container 12. Electrolytic action between the different metal chips in the device dissolves metal ions into the tank water preparatory to the next flushing. Any chlorine in the water will accelerate the electrolytic action, enhancing dissolution of metal ions into the water.

Device 10a produces results in toilet bowls similar to those described above for swimming pools. In one test of a toilet subjected to normal usage, no buildup of scum or stains developed over a four-month period in which device 10a was used. During that time interval no other effort was made to clean the toilet bowl. Without device 10a in its reservoir and subjected to similar usage, the same toilet accumulated a scum of algae and bacteria within approximately one week, necessitating cleaning at approximately one to two week intervals.

FIG. 4 EMBODIMENT

Referring to FIGS. 4 and 5, a second device 50 according to the invention comprises a container 52 adapted for standing upright on the floor of a swimming pool or toilet reservoir. Suspending means 14 is not used. Container 52 has a broad rectangular base 54 forming a floor in the container, generally trapezoidal opposite side walls 56, 58 and a rectangular upper wall 60 enclosing the top of the container. Openings 62 are provided in approximately the lower two-thirds of side walls 56, 58. Bottom wall 54 can also be perforated. The upper third of the side walls and top wall 60 are unperforated so as to retain an air bubble inside the container when device 50 is immersed in water. Chips of lead and copper fill the lower half to two-thirds of the container. The chips act as a ballast and, cooperating with the air bubble in the upper portion of the container, maintain the device in an upright position when it is dropped into a body of water. The broad base helps support the device in an upright position once it comes to rest on the bottom of the swimming pool or toilet tank.

Like devices 10, 10a, device 50 is preferably positioned near a water inlet or outlet so that water will circulate through the device into contact with the metal chips contained within.

Device 50 operates in substantially the same manner as devices 10, 10a and produces the same results.

Having shown and described my invention and two preferred embodiments thereof, it should be readily apparent that such embodiments can be modified in arrangement and detail without departing from the spirit of my invention.

I claim all such modifications and variations as come within the scope of the following claims.

1. A method for killing microorganisms including *E. coli* in a swimming pool, comprising:
   intermixed chips of at least two electrolytically reactive elemental metals from a group including zinc, copper and lead;
   immersing said chips in contact with one another into said pool;
   admitting water into interstices between said chips to electrolytically react the metals to produce a biocidal metal ion solution; and
   releasing said solution into said pool to kill microorganisms therein, including *E. coli*.

2. A method for killing microorganisms including *E. coli* in the bowl of a toilet, comprising:
   intermixing chips of at least two electrolytically reactive elemental metals from a group including zinc, copper and lead;
   immersing said chips in contact with one another into the tank of said toilet;
   admitting water into interstices between said chips to electrolytically react the metals to produce a biocidal metal ion solution; and
   releasing said solution into said toilet bowl to kill microorganisms therein, including *E. coli*.

3. A method for killing algae and coliform bacteria in a substantially closed body of water intended for use by vertebrates comprising: electrolytically reacting at least two elemental metals from a group including zinc, copper and lead in contact with said water to establish a biocidal solution effective to kill algae and coliform bacteria, the solution containing a dissolved ion concentration of each of said metals substantially less than an amount that would render the water unsafe for use by vertebrates including humans; the concentration of chlorine in said body of water being less than 0.1 milligrams per liter of water.

4. A method according to claim 3 in which lead and copper are reacted to produce a lead ion concentration in the water of less than 0.02 milligrams per liter and a copper ion concentration between 0.03 and 0.14 milligrams per liter.

* * * * *

UNITED STATES PATENT AND TRADEMARK OFFICE
CERTIFICATE OF CORRECTION

PATENT NO. : 4,416,854

DATED : November 22, 1983

INVENTOR(S) : JAMES W. NIELSEN

It is certified that error appears in the above–identified patent and that said Letters Patent are hereby corrected as shown below:

Column 6, line 47, "intermixed" should be --intermixing--.

Signed and Sealed this

Twenty-eighth Day of February 1984

[SEAL]

Attest:

GERALD J. MOSSINGHOFF

Attesting Officer

Commissioner of Patents and Trademarks